(12) United States Patent
Mahl

(10) Patent No.: US 9,351,814 B2
(45) Date of Patent: May 31, 2016

(54) DEVICE FOR ATTACHING OR REMOVING DENTAL OR SURGICAL COMPONENTS

(71) Applicant: Gregory Jay Mahl, Jericho, NY (US)

(72) Inventor: Gregory Jay Mahl, Jericho, NY (US)

(*) Notice: Subject to any disclaimer, the term of this patent is extended or adjusted under 35 U.S.C. 154(b) by 46 days.

(21) Appl. No.: 14/365,992

(22) PCT Filed: Dec. 16, 2012

(86) PCT No.: PCT/US2012/069975
§ 371 (c)(1),
(2) Date: Jun. 16, 2014

(87) PCT Pub. No.: WO2013/090872
PCT Pub. Date: Jun. 20, 2013

(65) Prior Publication Data
US 2014/0329200 A1   Nov. 6, 2014

Related U.S. Application Data

(60) Provisional application No. 61/576,554, filed on Dec. 16, 2011, provisional application No. 61/662,600, filed on Jun. 21, 2012.

(51) Int. Cl.
*A61C 8/00* (2006.01)
*A61B 17/28* (2006.01)
*A61C 3/00* (2006.01)

(52) U.S. Cl.
CPC .............. *A61C 8/0089* (2013.01); *A61B 17/282* (2013.01); *A61C 3/00* (2013.01); *A61C 8/00* (2013.01)

(58) Field of Classification Search
CPC ................................................... A61C 8/0089
USPC .............. 433/153, 154; 81/303–312
See application file for complete search history.

(56) References Cited

U.S. PATENT DOCUMENTS

| | | | | |
|---|---|---|---|---|
| 1,064,404 A | * | 6/1913 | Walker | A61C 7/04 433/4 |
| 1,094,269 A | * | 4/1914 | Taylor | A61C 3/16 433/154 |
| 2,040,713 A | * | 5/1936 | Shaffer | B25B 23/18 81/454 |
| 2,181,746 A | | 11/1939 | Siebrandt | |
| 3,852,884 A | * | 12/1974 | Lazarus | A61C 5/125 433/141 |
| 4,057,863 A | | 11/1977 | Bewley | |
| 4,976,617 A | * | 12/1990 | Carchidi | A61C 8/0089 433/141 |
| 5,026,376 A | | 6/1991 | Greenberg | |
| 5,120,221 A | * | 6/1992 | Orenstein | A61C 8/0089 433/159 |
| 5,626,474 A | * | 5/1997 | Kukla | A61C 8/0089 433/141 |

(Continued)

FOREIGN PATENT DOCUMENTS

WO   93/22975 A1   11/1993

OTHER PUBLICATIONS

International Search Report for PCT/US12/69975, mailed Mar. 1, 2013.

*Primary Examiner* — Ralph Lewis
(74) *Attorney, Agent, or Firm* — Stites & Harbison PLLC; Richard S. Myers, Jr.

(57) ABSTRACT

The present disclosure relates to a device for seating or orienting a component relative to a dental fixture. The device comprises three arms, each having a gripping surface, for holding said component, and the device further comprises a driver tube and a driver having an interchangeable tip for engaging the head of a screw for securing the component to the dental fixture.

14 Claims, 10 Drawing Sheets

(56) References Cited

U.S. PATENT DOCUMENTS

| | | |
|---|---|---|
| 6,021,343 A | 2/2000 | Foley |
| 2002/0031747 A1 | 3/2002 | Laster |
| 2004/0092928 A1 | 5/2004 | Sasso |
| 2004/0176779 A1 | 9/2004 | Casutt |
| 2008/0183179 A1* | 7/2008 | Siebel ............... A61B 17/8866 606/89 |
| 2011/0152953 A1* | 6/2011 | Link ............... A61B 17/1757 606/86 A |
| 2013/0071813 A1* | 3/2013 | Braegger ............ A61C 8/0089 433/173 |

* cited by examiner

DEVICE FOR ATTACHING OR REMOVING DENTAL OR SURGICAL COMPONENTS

TECHNICAL FIELD

The present disclosure relates to a device for seating, maintaining the orientation of or orienting an implant surgical component or an implant prosthetic component in or relative to a dental fixture. More particularly, the present disclosure relates to a device for attaching, orienting or removing an implant surgical component or prosthetic component relative to a dental fixture while simultaneously permitting manual screwing or unscrewing of the component to or from the dental fixture in the oral cavity. The present disclosure, without the use of the manual screwing or unscrewing function, is a multipurpose device for seating prefabricated posts and/or laboratory produced posts/cores into an endodontically treated tooth. The present disclosure, with the use of the manual screwing or unscrewing function, is directed to a multipurpose device for manipulating, attaching and/or removing, surgical components and prosthetic components for medical and/or dental applications.

BACKGROUND ART

There are numerous problems presented to clinicians as they position, seat or remove implant surgical components and prosthetic components (hereinafter "components") in the mouth of a patient. Generally, both of the clinician's hands are in the mouth of the patient; one hand holds a component in a seated configuration, and the other hand must hold the tool for securing such component. The confined nature of the oral cavity presents visual obstructions and contributes to reduced mobility and dexterity for the clinician. Further, accessing implants in the posterior oral cavity presents difficulties.

Significantly, the small size of dental components and the tools used to affix such components create an aspiration and/or swallowing hazard to the patient. Further, the gingival tissue itself can contribute to the loosening or rotation of components as such tissue expands during installation of a component in the implant.

Instruments that are traditionally used to affix and/or remove components, such as a hemostat and/or college pliers, can cause components to swivel or slip during handling and installation. For example, when a clinician applies pressure to a component when using the hemostat, such component has a tendency to slip from the hemostat. With college pliers, a component has a tendency to pivot with the application of force by the clinician. These deficiencies can contribute to the swallowing or aspiration hazards noted above.

Customized devices for installing or removing components may be designed by a laboratory for each patient; however, such devices are often cost prohibitive. Moreover, while devices exist to help a clinician properly place components, such devices may also contribute to the hazards that they are designed to prevent, thus forcing a clinician to use his hands to retrieve such components.

Accordingly, there exists a need in the art for a device that eliminates the use of small tools and known prosthetic tools and that is able to hold components, namely, abutments, impression copings/transfers, crowns, healing caps/screws and cover screws, as well as endodontic posts, thereby reducing the chance of patient aspiration or swallowing of such components during their insertion or removal. Further, in medical applications, there exists a need for a device that eliminates the need for facial incisions during mandibular surgery and additional anesthesia.

DISCLOSURE OF THE INVENTION

The present disclosure provides for a device that eliminates the use of previously known small instruments or tools when a clinician is manipulating, seating, orienting or removing dental or medical components. The device is able to hold components, namely, abutments, impression copings/transfers, crowns, healing caps/screws and cover screws, as well as endodontic posts, thereby reducing the chance of patient aspiration or swallowing of such components during their insertion or removal.

The present disclosure also provides for a device that enhances a clinician's dexterity because when using the device, both hands are not required to be in the patient's mouth while the clinician is manipulating, holding, seating, orienting and/or removing components. The present disclosure further provides a device that enables attachment and removal of components without the use of a clinician's fingers in the posterior of a patient's mouth. Indeed, the present disclosure provides for a device that removes the inherent structural problems of the gripping components of hemostats and college pliers.

The present disclosure provides for a device that is able to hold a component and a retaining screw in a proper orientation, relative to an implant, without interference from gingival or other body tissue(s), while securing or removing such component.

The present disclosure provides for a device that eliminates the need for a patient-specific, customized device, thereby reducing lab fees and appointment times.

The present disclosure further provides for a multifunctional device having at least three arms that seat (i.e. attach, place), maintain orientation of (position, register, align), screw (secure), unscrew, manipulate and/or remove (detach) components to or from a dental implant or medical appliance.

In some embodiments, the present disclosure provides a dental and medical device having hinged handles with interlocking ridges at a handheld end and at least three arms arranged in a triangular-shaped orientation, relative to one another, at a working end opposite the handheld end that are able to grip and orient components relative to a dental implant. In other embodiments, the disclosure provides a dental or medical device comprising: (i) a first handle comprising a first arm and a second arm; (ii) a second handle comprising a third arm; (iii) a joint that pivotally couples the first handle and the second handle; (iv) a riser connected to the first handle; and (v) a driver tube connected to the riser.

The device may be comprised of stainless steel. Moreover, its first and second arms may be arranged in a fixed orientation relative to one another, and it may comprise a third arm that is movable relative to the first and second arms. Further, the first arm may have an end portion that is angled downward at between about 65° and about 125° relative to a horizontal axis of the first handle. Similarly, the second arm may have an end portion that is angled downward at between about 65° and about 125° relative to a horizontal axis of the first handle. And in some embodiments, the third arm may have an end portion that is angled downward at between about 65° and about 125° relative to a horizontal axis of the first handle.

In certain embodiments, the driver tube may be adapted to receive a driver unit, which may be inserted into the driver tube, and the driver unit may comprise an interchangeable driver tip at a first end and a knob at a second end, and the driver tip may be adapted to engage the head of a screw.

The device may include a first handle that comprises a first locking portion joined to the first handle, wherein the first locking portion mates with a second locking portion that is joined to the second handle. Further, the first locking portion may comprise a first ridged surface, the second locking portion may comprise a second ridged surface, and the first ridged surface may be adapted to interlock with the second ridged surface. And the device may comprise a locking device operable to selectively retain the first and second handles in a fixed position relative to one another.

Further, in still other embodiments, the disclosure provides a dental clamp for gripping a component, the clamp comprising: (i) a first handle comprising a first arm and a second arm; (ii) a second handle comprising a third arm; (iii) a joint that pivotally couples the first handle and the second handle; (iv) a riser connected to the first handle; (v) a driver tube connected to the riser; (vi) a driver unit inserted through the driver tube; (vii) a locking portion connected to the first handle; and (viii) a locking portion connected to the second handle. The riser may comprise a cylindrical body portion. The driver unit may be longer than the driver tube. And an end portion of the driver tube may be angled in a downward direction approximately 95° relative to the longitudinal axis of the driver tube. Further, in some embodiments, the first arm of the dental clamp may have an end portion that is angled downward at between about 65° and about 125° relative to a horizontal axis of the first handle.

The present disclosure provides for a device that can be used in a method for minimally invasive fixation of a mandibular fracture by use of plates and screws. The device can be used without the need for an additional facial incision or tools to place screws for plate fixation.

The present disclosure further provides for a device that can be used in veterinary medicine.

It is to be understood that both the foregoing general description and the following detailed description present embodiments of the disclosure and are intended to provide an overview or framework for understanding the nature and character of the disclosure as it is claimed. The description serves to explain the principles and operations of the claimed subject matter. Other and further features and advantages of the present disclosure will be readily apparent to those skilled in the art upon a reading of the following disclosure.

BEST MODE FOR CARRYING OUT THE INVENTION

Figure 1:
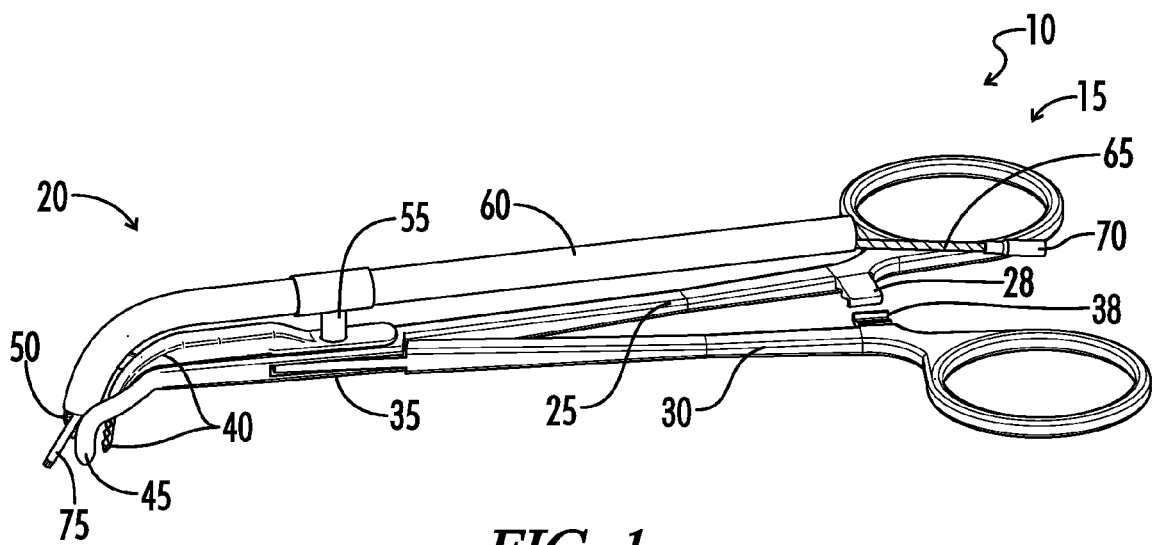
FIG. 1 shows a perspective view of the device according to the present disclosure.

Reference now will be made in detail to the embodiments of the present disclosure, one or more examples of which are set forth hereinbelow. Each example is provided by way of explanation of the device of the present disclosure and is not a limitation. In fact, it will be apparent to those skilled in the art that various modifications and variations can be made to the teachings of the present disclosure without departing from the scope of the disclosure. For instance, features illustrated or described as part of one embodiment can be used with another embodiment to yield a still further embodiment.

Thus, it is intended that the present disclosure covers such modifications and variations as come within the scope of the appended claims and their equivalents. Other objects, features and aspects of the present disclosure are disclosed in or are obvious from the following detailed description. It is to be understood by one of ordinary skill in the art that the present discussion is a description of exemplary embodiments only and is not intended as limiting the broader aspects of the present disclosure.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods and device(s) of the present disclosure, including components thereof, can comprise, consist of, or consist essentially of the essential elements and limitations of the embodiments described herein, as well as any additional or optional components or limitations described herein or otherwise useful in dental and/or medical applications.

Terms such as "left," "right," "up," "down," "bottom," "top," "front," "back," "forward," "backward," "in," "out" and the like are applicable to the embodiments shown and described in conjunction with the drawing. These terms are merely for the purposes of description and do not necessarily apply to the position in which the device may be constructed or used.

As used herein, the term "about" should be construed to refer to both of the numbers specified as the endpoint(s) of any range. Furthermore, any reference to a range should be considered as providing support for any subset within that range.

Referring to the figures, particularly to FIG. 1, a device according to the present disclosure is shown and referenced by reference numeral 10. In some embodiments, the device 10 is a dental clamp, a surgical clamp or other clamping device. Device 10 has a scissor-like or forceps-like configuration with a hand held end 15 and a working end 20. Device 10 has a first handle 25 and a second handle 30, wherein the first handle 25 and the second handle 30 are connected at a joint comprising a hinge or pivot 35. In some embodiments, the first handle 25 and the second handle 30 are maintained in a pivotal relationship by means of a pivot pin. In other embodiments, a joint, hinge or pivot connection of the two handles is pinless. The first handle 25 and second handle 35 may be connected by any means known in the art. In some embodiments, the first handle 25 and the second handle 35 are separable to allow for effective sterilization of the device. In certain embodiments, the device is comprised of stainless steel or other readily resterilizable material.

First handle 25 has two fixed arms, namely a center arm 40 and a side arm 45, that remain in a fixed orientation relative to one another. Second handle 30 is able to pivot relative to first handle 25 and has a movable side arm 50. A riser 55 is connected to first handle 25. In certain embodiments, the riser 55 is further connected to the second handle. In some embodiments, the riser 55 comprises a riser body that is hollow and/or that comprises an opening, void or hole therethrough. Indeed, in certain embodiments, the riser comprises a cylindrical-shaped opening that traverses the length of the riser body. A driver tube 60 is rigidly held by the riser 55 or adjacent to the riser 55 in a fixed position relative to first handle 25. In certain embodiments, the driver tube passes through the opening, void or hole in the riser body and may be rigidly attached thereto. Driver tube 60 contains a driver 65. In some embodiments, the overall length of the device 10 can range from between about 4.5 inches and about 9.0 inches (about 11.43 cm to about 22.86 cm) depending upon the location of the installation and other factors. Moreover, in some embodiments, the length of the driver tube 60 is between about 3 inches and about 7.5 inches (about 7.6 cm to about 19 cm). And in some embodiments, the length of the driver is between about 8 cm and about 18 cm. In certain embodiments, the length of the device 10 is between about 5.25 and about 6.75 inches (about 13.3 cm to about 17.1 cm). In a particular embodiment, the length of the device 10 is about 5.5 inches (about 14 cm). The length and other dimensions of the device 10 may be adapted, as appropriate, for the desired dental or medical application, as known in the art.

Figure 2A:
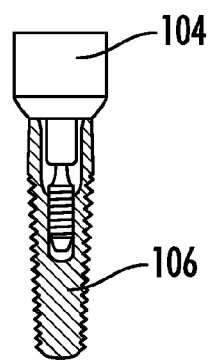
FIGS. 2*a*, 2*b*, 2*c* and 2*d* show examples of components that are used with the device of FIG. 1.
Figure 2B:
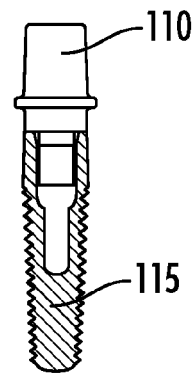
Figure 2C:
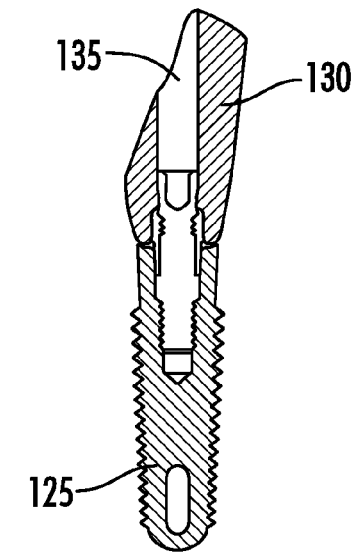
Figure 2D:
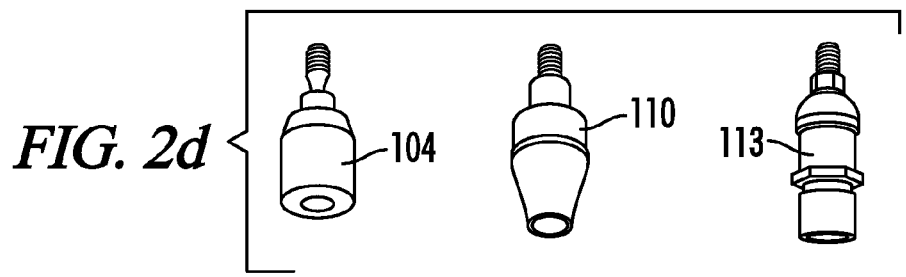

Referring to FIGS. 2a 2b, 2c, and 2d, examples of some of the components 100 that may be seated, placed or otherwise manipulated by the device of the present disclosure are shown therein. FIG. 2a shows a healing cap 104 disposed within implant 106. FIG. 2b shows an abutment 110 secured within an implant 115. FIG. 2c illustrates a cross section of an abutment 130 secured within an implant 125 with a retaining screw 135. Retaining screw 135 is secured in place with driver 75 of device 10 of FIG. 1. FIG. 2d illustrates a healing cap 104, an abutment 110 and a transfer coping 113.

Figure 3:
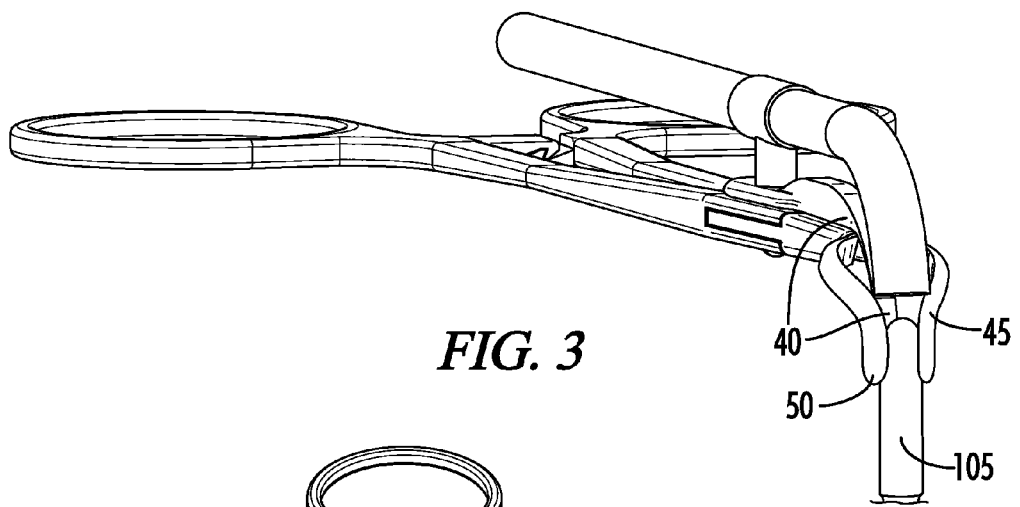
FIG. 3 shows a front perspective view of the device of FIG. 1 holding an endodontic post.

Referring to FIG. 3, center arm 40, side arm 45 and movable side arm 50 of device 10 are disposed in a triangulated relationship to permit secure holding of a component, such as a healing cap 104, an abutment 110, a retaining screw 135, a transfer coping 113 or an endodontic post, in a secure fashion. Indeed, device 10 is structured to hold components 100, such as healing cap 104, abutments 110 and 130, and endodontic posts 105 between triangulated arms 50, 40 and 45 of working end 20 to prevent the accidental slipping of components that is often experienced with two-armed college pliers or hemostats. In certain embodiments, the term "triangulated" means arranged in a triangular fashion or in a triangular-shaped arrangement.

Figure 4:
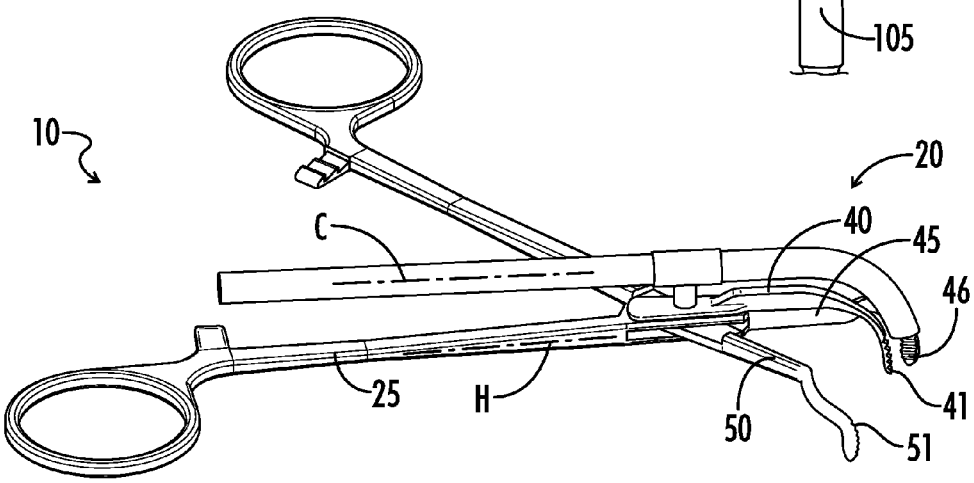
FIG. 4 shows front perspective view of the device of FIG. 1 in an opened configuration.
Figure 5:
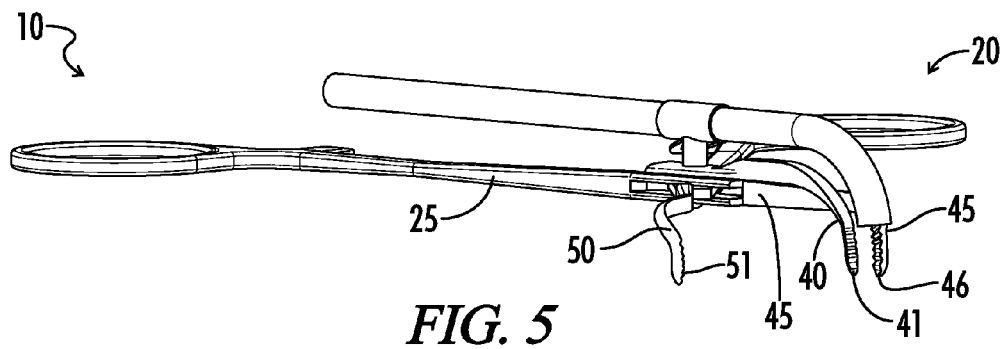
FIG. 5 shows a close-up front perspective view of the device of FIG. 1 in an opened configuration.

Referring to FIGS. 4 and 5, working end 20 of device 10 includes a center arm 40, a side arm 45 and a movable side arm 50. Arms 40, 45, and 50 each have a gripping surface, 41, 46 and 51, respectively, for contacting and gripping components 100 when device 10 is used. In some embodiments, gripping surfaces 41, 46, and 51 are flat, serrated surfaces having at least one rounded edge. In other embodiments, gripping surfaces 41, 46 and 51 are concave to facilitate holding of components 100. In some embodiments, the gripping surfaces 41, 46 and 51 of triangulated arms 50, 40 and 45 of working end 20 are positioned such that the outer edges of each of the gripping surfaces 41, 46 and 51 are arranged at the apexes of a triangle-shaped space formed therebetween.

In certain embodiments, arms 40, 45 and 50 have rounded tips to ensure comfort for a patient during insertion and to facilitate movement within the patient's oral cavity. As shown in FIG. 4, in some embodiments arms 40 and 45 each have a downward angle of approximately 95° relative to the horizontal axis (H) of first handle 25. Moreover, in some embodiments, each of arms 40 and 45 may have a downward angle of between about 90° and about 100° relative to the horizontal axis (H) of first handle 25. While arms 40, 45 and 50 are shown having an approximately 95° angle, such angle with handle axis (H) can range from about 65° to about 125°.

Each of arms 40, 45 and 50 has an end portion nearer the working end of the device and an end portion nearer the handling end of the device. In some embodiments, the end portion of any or all of arms 40, 45 and 50 may be bent or curved downward, relative to the horizontal axis (H) of the first handle, at an angle of between about 65° and about 125°. In some embodiments, any of arms 40, 45 and 50 may have an end portion nearer the working end of the device that is bent or curved downward relative to the horizontal axis (H) of the first handle at an angle of about 95°.

Flat gripping surfaces 41, 46 and 51, coupled with the angle of arms 50, 40 and 45 ensure a large contact surface between the outer surface of a component 100 and the gripping surfaces 51, 46 and 41. This contact prevents slipping or pivoting of components 100 from the grasp of device 10, as is often experienced with college pliers or hemostats.

Side arm 45 and movable side arm 50 are curved outwardly from the central longitudinal axis of the device for clearance around driver tube 60 and implant components 100 of FIGS. 2a 2b, 2c, and 2d or endodontic post 105, as shown in FIG. 3. In some embodiments, side arm 45 has a semi-circular shape that is complementary to a semi-circular shape of movable side arm 50. When the side arm 45 and movable side arm 50 are opposite one another, a generally cylindrical space is formed between them. Arms 40, 45 and 50 are preferably made from high carbon stainless steel and have a degree of flexibility to firmly grip components or endodontic posts during insertion.

Figure 6:
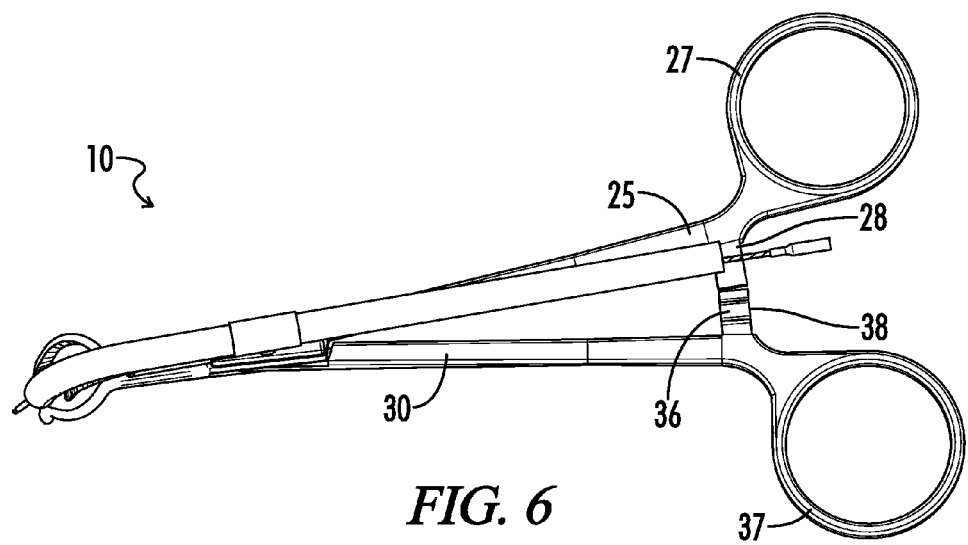
FIG. 6 shows a top view of the device of FIG. 1 in a locked configuration.

Referring to FIG. 6, first handle 25 and second handle 30 of device 10 are shown in a closed and locked configuration. First handle 25 and second handle 30 have finger grips 27 and 37, respectively, to enable a clinician to easily manipulate device 10. First handle 25 has a locking portion 28 that mates with a locking portion 38 of second handle 30 via interlocking ridges 26 (not shown) and 36, respectively.

Bringing finger grip 27 closer to finger grip 37, such as during a squeezing motion, engages ridges 26 and 36 to lock tags 28 and 38, and therefore handles 25 and 30. When handles 25 and 30 are locked, and specifically when ridges 26 are engaged with ridges 36, center arm 40, side arm 45 and movable side arm 50 are in a fixed position relative to each other to engage and hold component 100 or an endodontic post 105. When handles 25 and 30 are locked, the clearance or distance between side arms 45 and 50 is variable within the limits of the model of device 10 used, which, in certain embodiments, as in FIG. 1, is approximately 2 mm. This clearance permits engagement of the largest diameter of a component by center arm 40. In certain embodiments, the clearance permits engagement of a component having a diameter in the range of about 2 mm to about 10 mm. In some embodiments, the device engages a component having a diameter of between about 2 mm and about 6 mm. In other embodiments, the device is adapted to engage a component having a diameter of between about 1.9 mm and about 4.8 mm. In a particular embodiment, the device engages a component having a diameter of about 6.5 mm.

Figure 18:
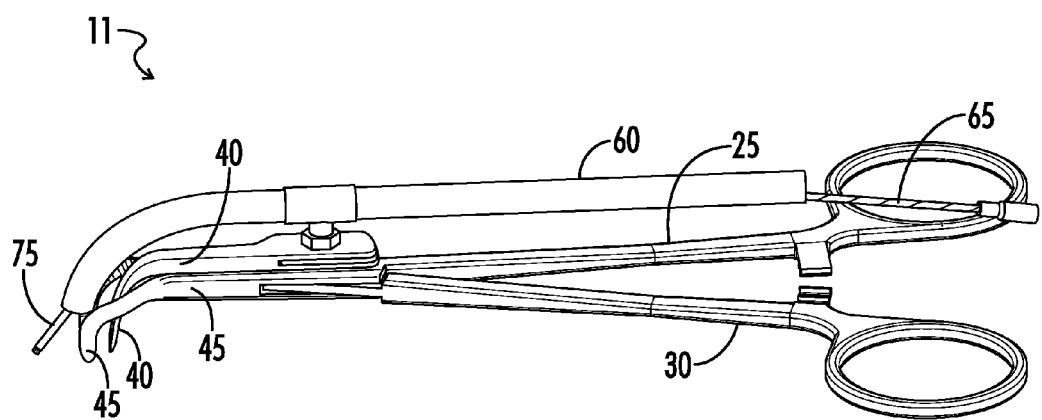
FIG. 18 shows a device according to the present disclosure that has a larger spacing between arms than that of the embodiment shown in FIG. 1.

Handles 25 and 30 are released from the locked configuration by slightly pressing together handles 25 and 30 and thereby releasing locking portion 28 from portion 38. Device 10 can be designed to permit a larger clearance such as up to about 10 mm to handle larger components 100, as shown in FIG. 18. In FIG. 18, device 11 has a larger clearance between arms 40, 45 and 50 for grasping components than does device 10 of FIG. 1.

Figure 7:
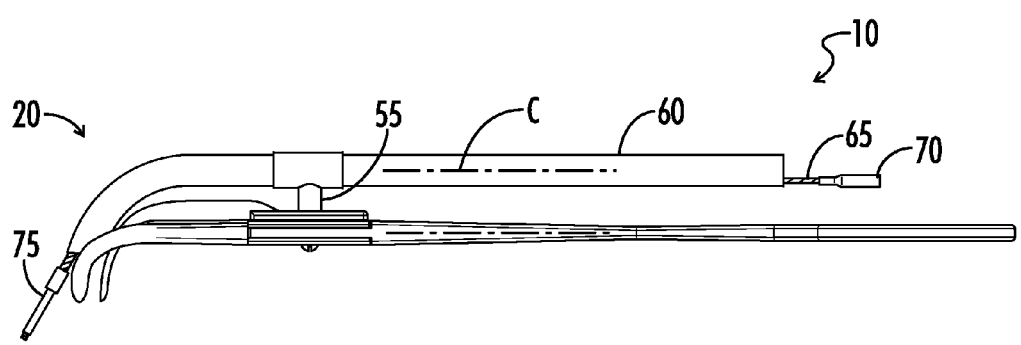
FIG. 7 shows a side view of the device of FIG. 1.
Figure 8:
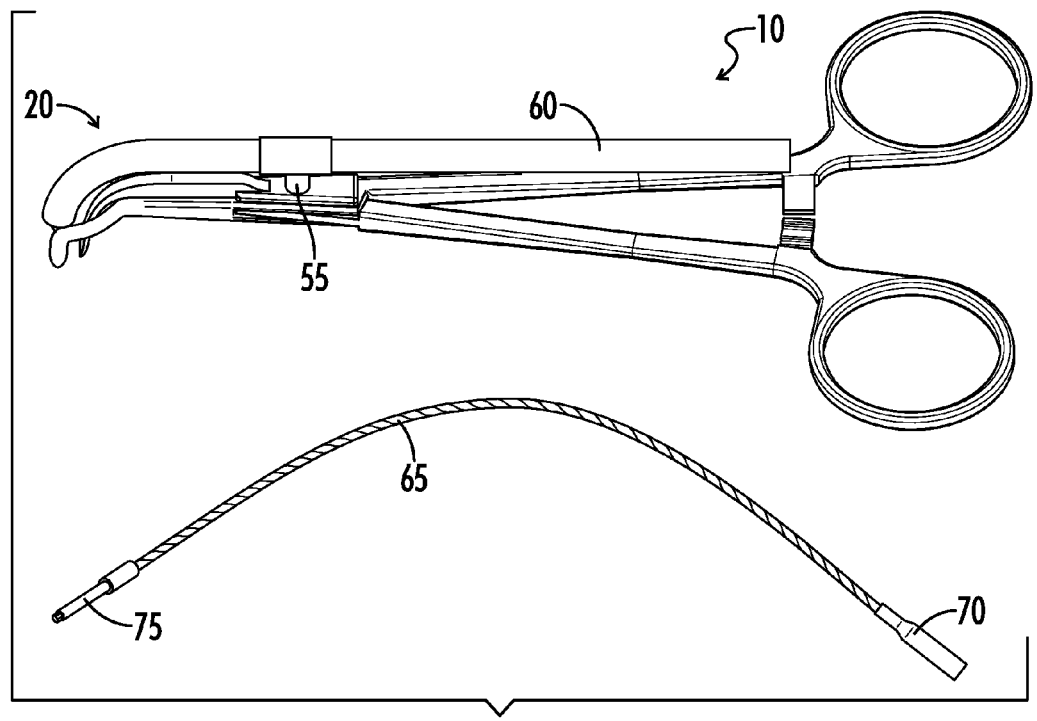
FIG. 8 shows device of FIG. 1 with the interchangeable driver unit removed from the driver tube.

Referring to FIGS. 1, 7 and 8, device 10 includes a riser 55, a driver tube 60 and a driver portion. In certain embodiments, the driver portion is composed of a knob 70, driver unit 65 and a driver tip 75. Riser 55 extends in a perpendicular fashion from first handle 25 and holds driver tube 60. In some embodiments, riser 55 and driver tube 60 may be held together rigidly by any means known in the art.

In some embodiments, riser height ranges from about 0.094 inches to about 0.41 inches (about 0.24 cm to about 1.04 cm) to provide optimal clearance to opposing dentition and ease of knob rotation. As shown in FIG. 7, at the working end 20 of device 10, driver tube 60 is angled approximately 95° (in a downward direction) relative to the longitudinal axis (C) of tube 60. In some embodiments, driver tube 60 can be angled in a range of from about 65° to about 125° relative to the longitudinal axis (C) of tube 60 to easily enable manipulation of driver unit 65 inside of driver tube 60 when retaining screws are being manipulated. Some other purposes of this angle are to permit insertion of driver unit into driver tube, to reduce "spring back" of the driver tip when engaging a retaining screw and to provide clearance to opposing dentition.

Driver tube 60 is preferably fixed to riser 55 to provide stability when knob 70 of driver unit 65 is twisted or manipulated to secure a component 100 to an implant device. In various embodiments, driver tube 60 can be fixed, it can slide, or it can rotate or move relative to riser 55, depending upon the embodiment of the device that is used. In certain embodiments, to ensure patient comfort and safety, driver tube 60 comprises a smooth outer surface.

Figure 9:
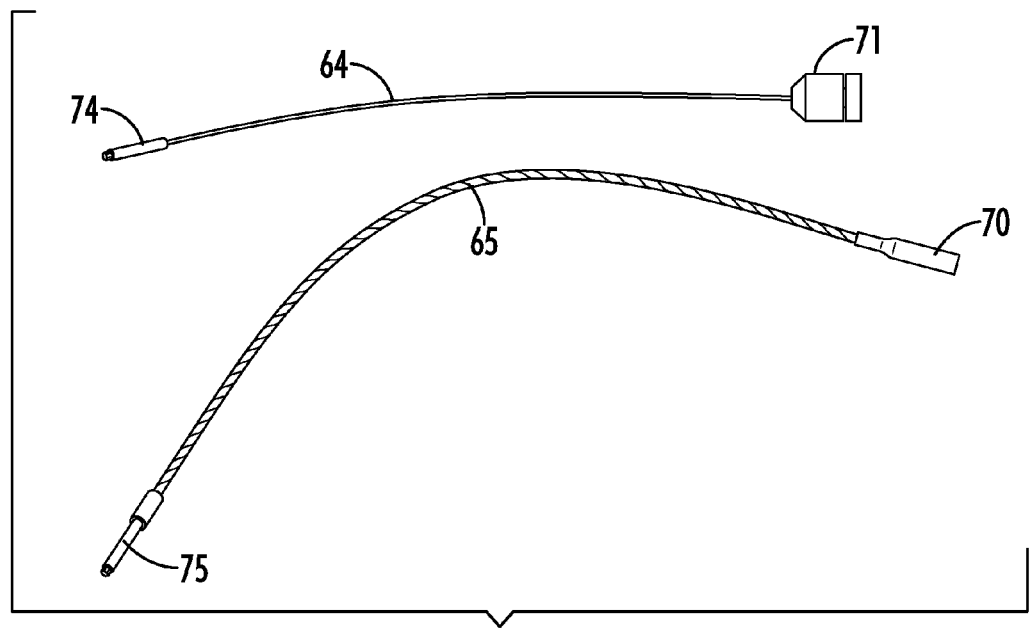
FIG. 9 shows an alternative driver unit embodiment.
Figure 10:
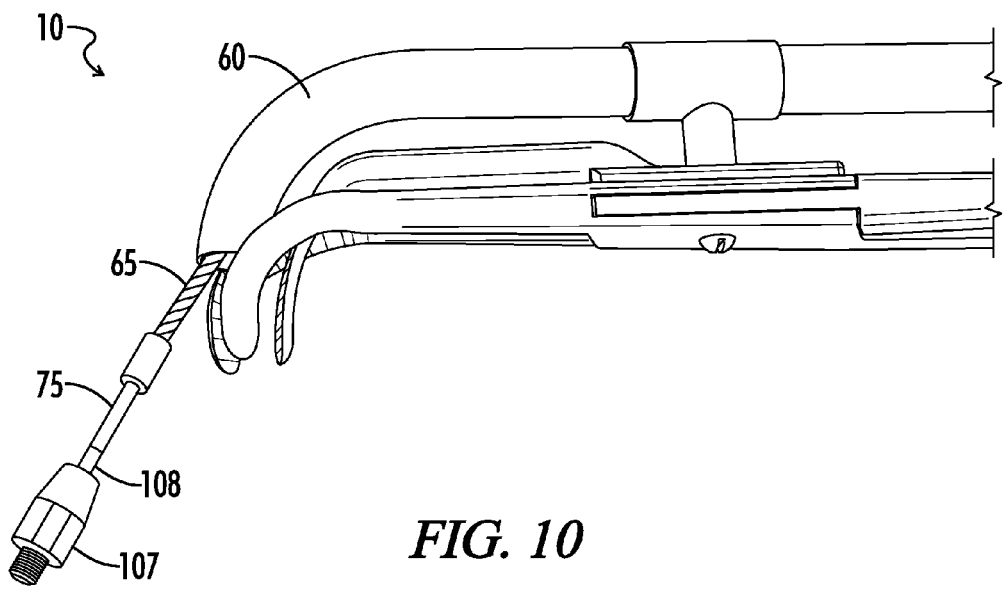
FIG. 10 shows the device of FIG. 1 seating a driver tip into an abutment retaining screw.
Figure 11:
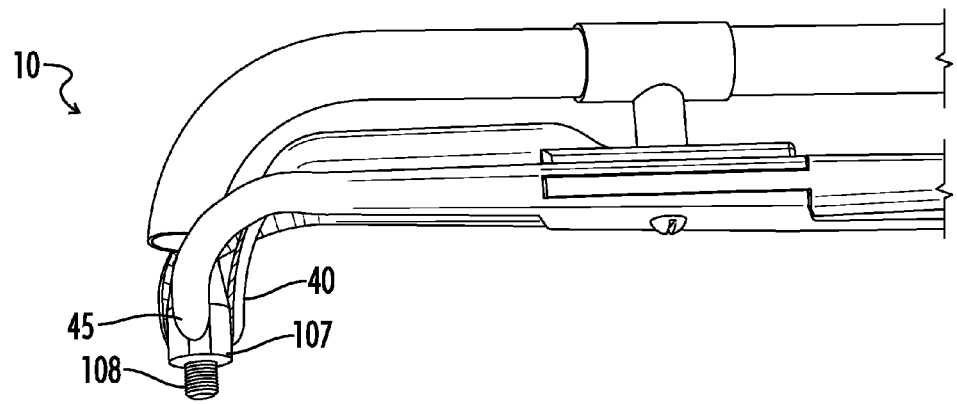
FIG. 11 shows the device of FIG. 1 in a locked configuration with an abutment before installing retaining screw into implant.

Referring to FIGS. 7, 8 and 9, an interchangeable driver tip unit is shown with driver tube 60. Driver unit 65 has a knob 70 at one end to assist in manipulating driver tip 75 at opposite end of driver unit 65. In some embodiments, the driver unit 65 has a greater length (i.e. is longer than) than the driver tube 60. Driver tip 75 engages a head of a retaining screw to position the screw within a component of a dental fixture. When knob 70 is rotated, driver tip 75 rotates in the retaining screw, and in particularly in the head of retaining screw, to seat such screw in a component. In certain embodiments, when knob 70 is rotated, driver tip 75 rotates, thereby causing the retaining screw to rotate whilst the driver tip 75 engages the head of a retaining screw. Accordingly, in some embodiments, driver unit 65 is constructed in a braided configuration because such structure enables torque to be effectively transmitted from knob 70 to driver tip 75. In certain embodiments, driver unit 65 has a length of between about 8 cm and about 18 cm, and it may comprise several strands of wound wire that provide a degree of flexibility yet strength to transmit torque to driver tip 75.

In certain embodiments, driver tip 75 may be interchangeable so that the device can function with a variety of components having particular configurations of shape and size and so that each respective driver tip 75 can mate with differing cross sections of retaining screw heads. For example, in one embodiment, driver tip 75 can be shaped and sized to mate with a hexagonal head of a retaining screw. In another embodiment, driver tip 75 may be shaped and sized to mate with a triangular head of a retaining screw.

In some embodiments, device 10 could have different, interchangeable driver units with varying cross sections to accommodate different screw head cross-sections, as shown in FIG. 9 at reference numerals 64 and 65. A driver unit of FIGS. 1, 6, 7 and 8 is shown comprising wound wire having a knob 70 and a driver tip 75. In a particular embodiment, driver unit 64 comprises a flexible nylon that is able to transmit torque from knob 71 to driver tip 74. In some embodiments, driver unit 64 comprises flexible, braided or solid wire of stainless steel, nylon or other readily resterilizable material(s). Knobs can have different cross-sections depending upon the preference of the user, as shown in FIG. 9.

Figure 12:
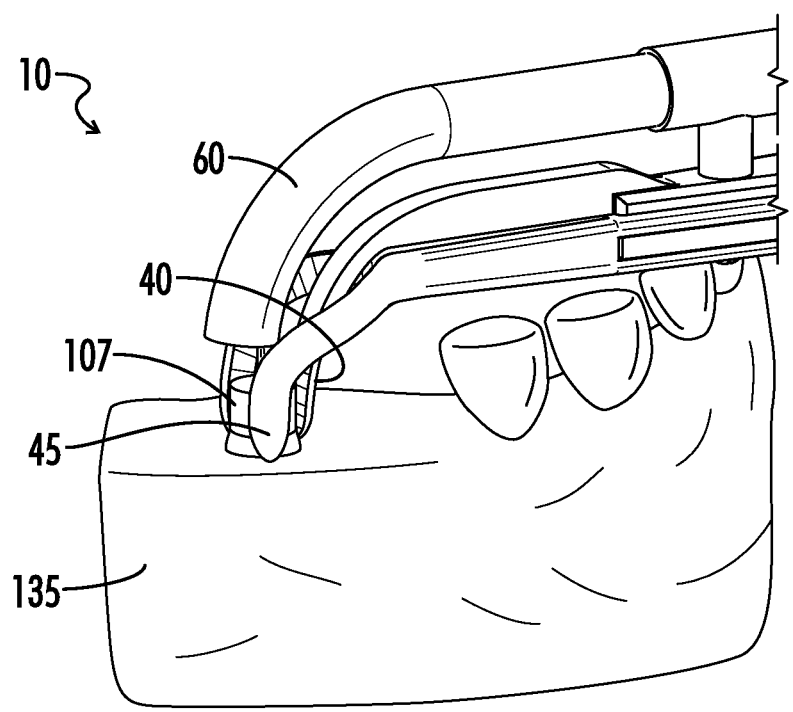
FIG. 12 shows the device of FIG. 1 seating an abutment onto an implant analog model.
Figure 13:
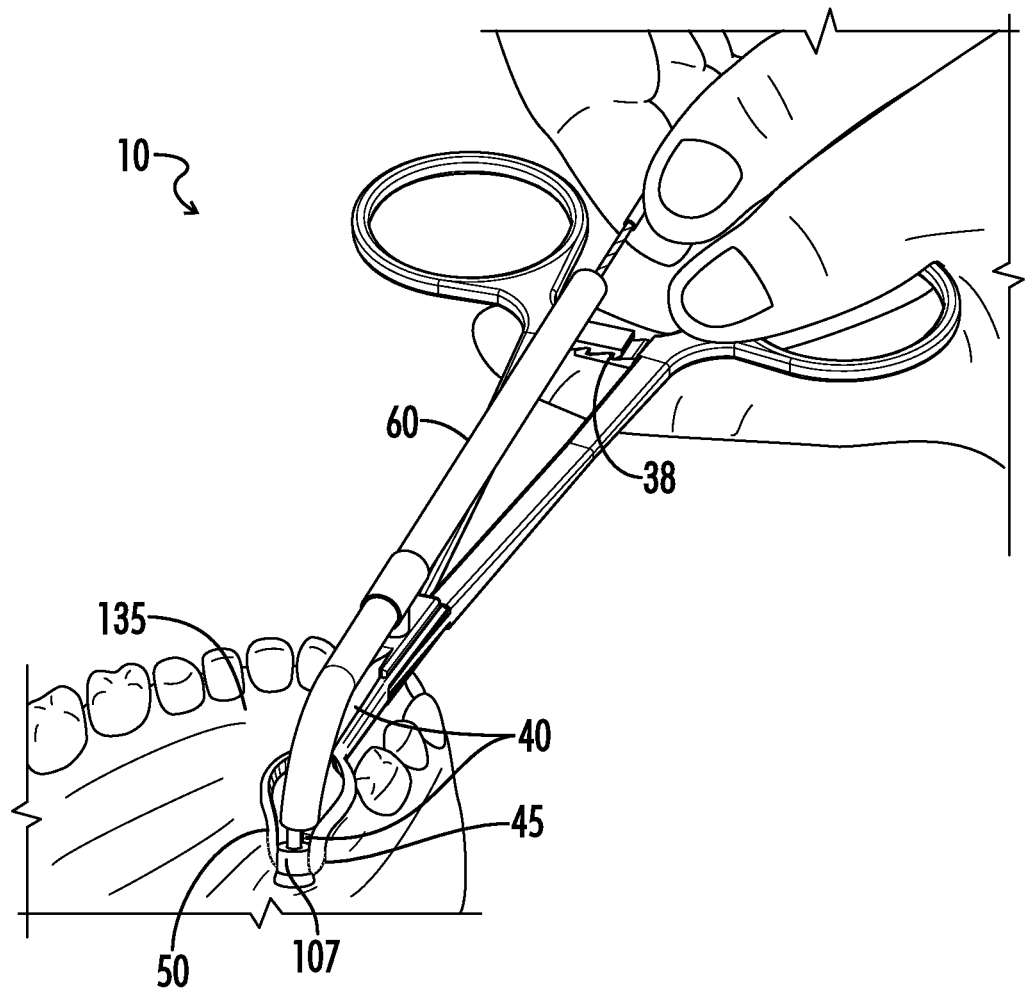
FIG. 13 shows the device of FIG. 1 screwing an abutment to an implant analog model.

Referring to FIGS. 7, 10, 11, 12 and 13, the operation of the device will be described with respect to an abutment 107 as the component. In operation, driver knob 70 is pushed through driver tube 60 toward working end 20 to seat driver tip 75 into an abutment retaining screw 108. Abutment 107 is placed between arms 40, 45 and 50, and device 10 is locked. Abutment 107 is seated into an implant in the mouth of a patient with device 10 and is maintained in the mouth with device 10 still in a locked configuration. A clinician then pushes knob 70 to establish contact between retaining screw 108 and the implant and rotates knob 70 until resistance is felt between the implant and the retaining screw. Clinician can then unlock device 10 by unlocking tabs 28 and 38 and then fully tighten retaining screw 108 with a hand driver or a torque wrench, as needed. FIGS. 12 and 13 show such a process conducted on a model 135 for purposes of visibility.

Figure 14:
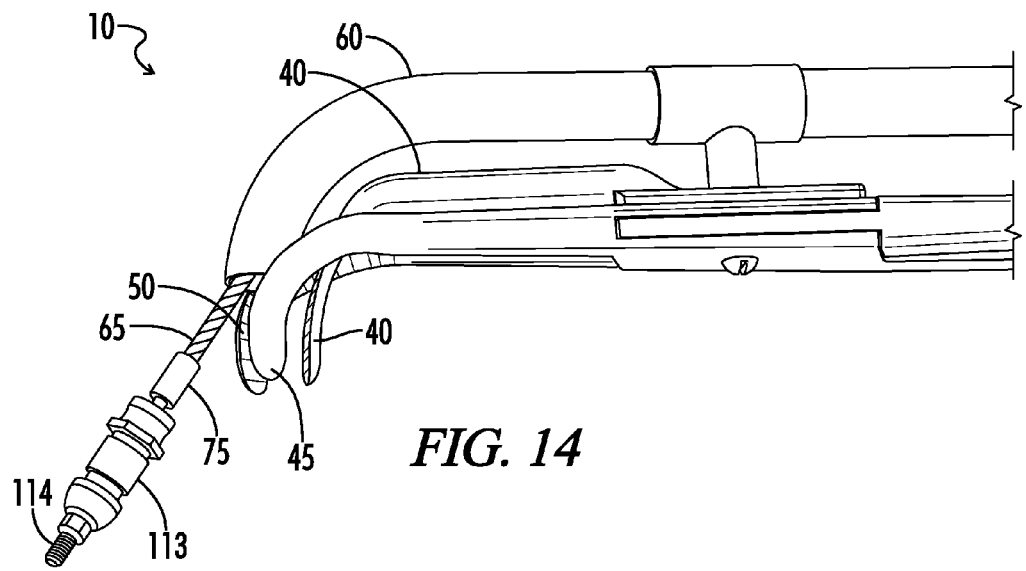
FIG. 14 shows the device of FIG. 1 seating a driver tip into an impression transfer retaining screw.
Figure 15:
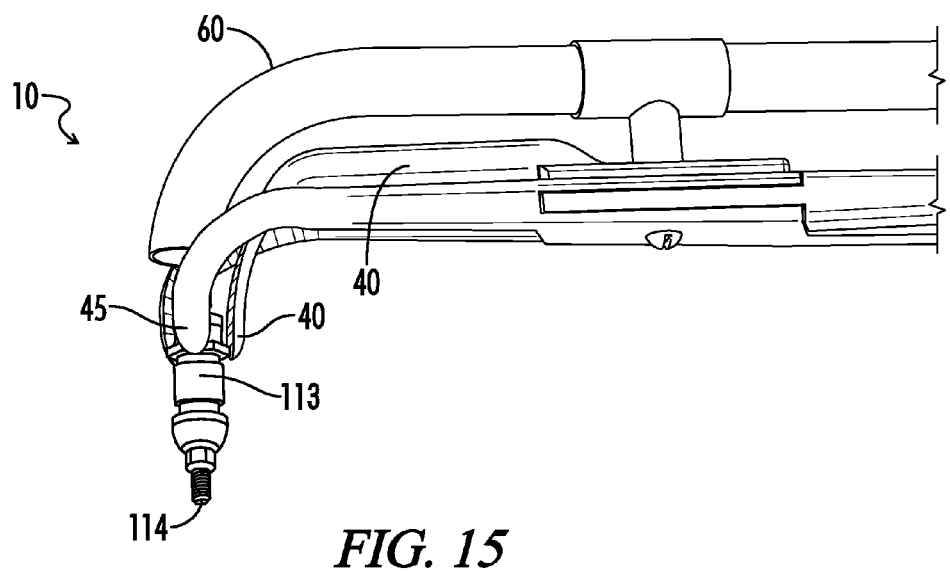
FIG. 15 shows the device of FIG. 1 in a locked configuration with an impression transfer before installing into an implant.

Referring to FIGS. 14 and 15, device 10 can also be used for seating an impression transfer 113 into an implant. In some embodiments, a clinician pushes knob 70 forward, toward working end 20, to seat driver tip 75 into a retaining screw 114. Transfer 113 is placed between arms 40, 45 and 50 and device 10 is placed in a locked configuration. The clinician then pushes retaining screw 114 flush with transfer apex configuration. The clinician then sets transfer 113 into the implant in the patient's mouth with device 10 and holds such position in the mouth. Clinician pushes knob 70 to establish contact between retaining screw 114 and the implant and rotates knob 70 until resistance is felt between retaining screw 114 and the implant. In some embodiments, the clinician may pull knob 70 backward, toward the handheld end of device 10 to wholly or partially withdraw driver unit 65 from retaining screw 114. Clinician can then unlock device 10 by unlocking tabs 28 and 38, remove the device from the patient's mouth and subsequently fully tighten the retaining screw with a hand driver or a torque wrench, as needed.

In some embodiments, device 10 can also be used for seating a crown in an implant having a retaining screw. A clinician pushes knob 70 forward to seat a driver tip 75 into the crown retaining screw. The crown is pushed into arms 40, 45 and 50 and the device is placed in a locked configuration.

The clinician then pushes retaining screw flush with the crown apex configuration. The clinician then sets the crown into the implant in the patient's mouth with device 10 and holds such position in the mouth. The clinician pushes knob 70 to establish contact between the retaining screw and the implant and rotates knob 70 until resistance is felt between the crown retaining screw and the implant. The clinician can then unlock device 10 by unlocking tabs 28 and 38, remove the device from the patient's mouth and then fully tighten the retaining screw with a hand driver or a torque wrench, as needed. When seating crowns that are located in the posterior portion of the mouth, arms 40, 45, and 50 must clear proximal surfaces due to the buccal or lingual placement of the crown.

Figure 16:
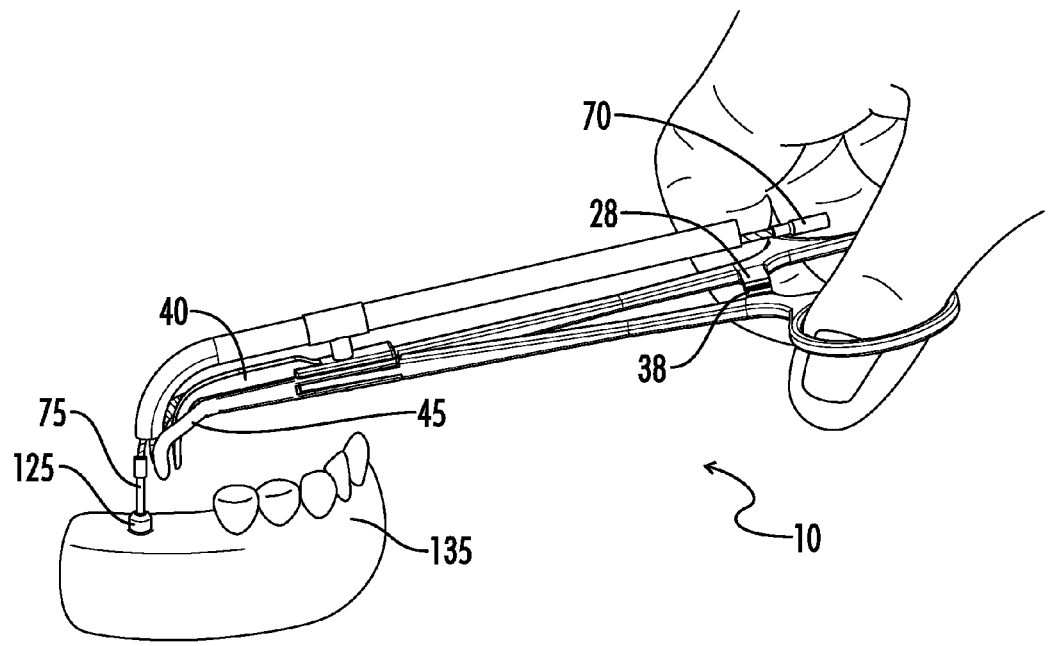
FIG. 16 shows the device of FIG. 1 with driver tip inserted into a healing cap on an implant analog model.
Figure 17:
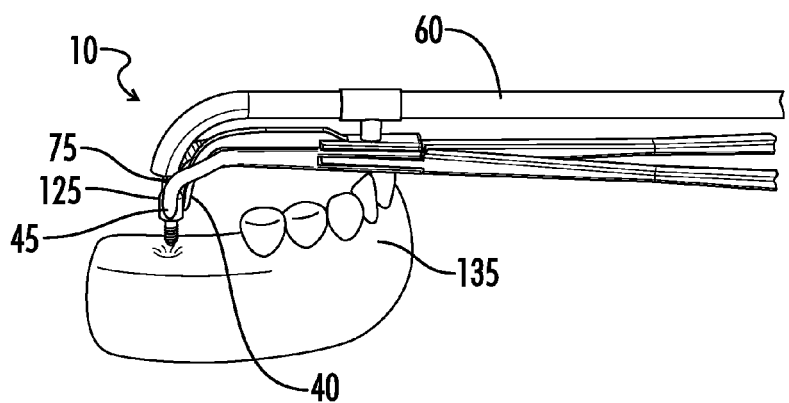
FIG. 17 shows the device of FIG. 1 with a removed healing cap.

Referring to FIGS. 16 and 17, device 10 can also be used for removing a previously installed healing cap 125. In some embodiments, a hand driver or a torque wrench can first be used to slightly loosen the healing cap 125. A clinician pushes knob 70 to seat the driver tip 75 into the healing cap 125. The clinician can either hold or lock device 10 to keep arms 40, 45, and 50 loose as a cage to permit healing cap 125 to rotate in arms. The clinician can turn knob 70 to unscrew the healing cap 125. The clinician may then fully lock device 10 around the healing cap 125 to remove the healing cap 125 from mouth of patient. FIGS. 16 and 17 show such a process conducted on a model 135.

In addition to the dental application for the device described herein, the device of the present disclosure has surgical applications as well as applications in veterinary medicine. For example, the device may be used for minimally invasive fixation of mandibular fractures (i.e. angle and ramus) by using plates and screws. The device can be used without the need for an additional facial incision to place screws for plate fixation. The intraoral approach is more efficient than the extraoral approach and can be performed under local anesthesia. The intraoral approach is a quicker procedure that eliminates the need for a facial incision and therefore, any resultant scaring and possible nerve damage.

Further, the device also has application in veterinary medicine, when handling and treating animals.

It should be understood that the foregoing description is only illustrative of the present disclosure. Various alternatives and modifications can be devised by those skilled in the art without departing from the disclosure. Accordingly, the present disclosure is intended to embrace all such alternatives, modification and variances that fall within the scope of the present disclosure. In addition, it should be understood that aspects of the various embodiments may be interchanged in whole or in part. For example, while specific embodiments of devices for dental and/or surgical applications have been exemplified, other embodiments and uses are also contemplated herein. Therefore, the spirit and scope of the appended claims should not be limited to the description of the versions contained therein.

What is claimed is:

1. A dental or medical device comprising a working end, a handheld end and a horizontal axis (H), and:
   (i) a first handle comprising a first arm and a second arm, the first and second arms having end portions angled downward relative to the horizontal axis;
   (ii) a second handle comprising a third arm, the third arm having an end portion that is angled downward relative to the horizontal axis;
   (iii) a joint that pivotally couples the first handle and the second handle;
   (iv) a riser connected to the first handle; and
   (v) a driver tube connected to the riser, the driver tube being adapted to receive a driver unit, and said driver tube having a handheld end length along the horizontal axis and beyond the pivot a working end length angled downward toward the working end to direct the driver unit toward a space between at least two arm end portions.

2. The device of claim 1, wherein the device is comprised of stainless steel.

3. The device of claim 1, wherein the first and second arms are in a fixed orientation relative to one another.

4. The device of claim 3, wherein the third arm is movable relative to the first and second arms.

5. The device of claim 1, wherein the first arm has an end portion that is angled downward at between about 65° and about 125° relative to a horizontal axis of the first handle.

6. The device of claim 1, wherein the second arm has an end portion that is angled downward at between about 65° and about 125° relative to a horizontal axis of the first handle.

7. The device of claim 1, wherein the third arm has an end portion that is angled downward at between about 65° and about 125° relative to a horizontal axis of the first handle.

8. The device of claim 1, wherein the driver unit comprises a driver tip at a first end and a knob at a second end.

9. The device of claim 1, wherein the driver unit is inserted into the driver tube.

10. The device of claim 1, wherein the driver tip is interchangeable.

11. The device of claim 1, wherein the driver tip is adapted to engage the head of a screw.

12. The device of claim 1, wherein the first handle comprises a first locking portion joined to the first handle that mates with a second locking portion that is joined to the second handle.

13. The device of claim 12, wherein the first locking portion comprises a first ridged surface, the second locking portion comprises a second ridged surface, and further wherein the first ridged surface is adapted to interlock with the second ridged surface.

14. The device of claim 1, further comprising a locking device operable to selectively retain the first and second handles in a fixed position relative to one another.

* * * * *